United States Patent [19]
Routh et al.

[11] Patent Number: 5,766,230
[45] Date of Patent: Jun. 16, 1998

[54] PACEMAKER WITH INTRA-STIMULUS CAPTURE DETECTION

[75] Inventors: André Guy Routh, Lake Jackson; Don Curtis Deno, Missouri City; William Bruce Rottenber, Lake Jackson, all of Tex.

[73] Assignee: Sulzer Intermedics Inc., Angleton, Tex.

[21] Appl. No.: 744,577

[22] Filed: Nov. 6, 1996

[51] Int. Cl.⁶ .................................................. A61N 1/365
[52] U.S. Cl. .................................................. 607/27; 607/28
[58] Field of Search .................................. 607/27, 28

[56] References Cited

U.S. PATENT DOCUMENTS

| | | |
|---|---|---|
| 3,920,024 | 11/1975 | Bowers . |
| 4,373,531 | 2/1983 | Wittkampf et al. . |
| 4,674,508 | 6/1987 | DeCote . |
| 4,762,136 | 8/1988 | Baker, Jr. . |
| 4,817,605 | 4/1989 | Sholder . |
| 4,821,724 | 4/1989 | Whigham et al. . |
| 4,878,497 | 11/1989 | Callaghan et al. . |
| 4,895,152 | 1/1990 | Callaghan et al. . |
| 4,955,376 | 9/1990 | Callaghan et al. . |
| 5,161,529 | 11/1992 | Stotts et al. . |
| 5,324,310 | 6/1994 | Greeninger et al. ............ 607/28 |
| 5,330,512 | 7/1994 | Hauck et al. .................. 607/28 |

OTHER PUBLICATIONS

Alt, E., C. Kriegler, P. Fotuhi, R. Willhaus, W. Combs, M. Heinz, and D. Hayes, "Feasibility of Using Intracardiac Impedance Measurements for Capture Detection," PACE (Nov., Part II, 1992), 15:1873–1879.

Auerbach, A. and S. Furman, "The Autodiagnostic Pacemaker," PACE (Jan.–Feb. 1979), 2:58–68.

Boltz, A., M. Hubmann, R. Hardt, J. Riedmuller, and M. Schaldach, "Low Polarization Pacing Lead for Detecting the Ventricular–evoked Response," Medical Progress through Technology (1993), 19:129–137.

Boute, W., G. Cals, P. Heijer, and F. Wittkampf, "Morphology of Endocardial T–Waves of Fusion Beats," PACE (Nov. 1988, Part II), 11:1693–1697.

Curtis, A.B., S. Maas, A. Domijan, Jr., S. Keim, and A. Duran, "A Method for Analysis of the Local Atrial Evoked Response for Determination of Atrial Capture in Permanent Pacing Systems," PACE (Nov. 1991, Part I), 14:1576–1581.

Curtis, A.B., F. Vance and Miller–Shifrin, K., "Characteristic Variation in Evoked Potential Amplitude with Changes in Pacing Stimulus Strength," The American Journal of Cardiology, 66:416–422.

Donaldson, R. and A. Rickards, "The Ventricular Endocardial Paced Evoked Response," PACE (Mar.–Apr. 1983, Part I), 6:253–259.

Dreifus, L., "In Search of Atrial Sensing and Capture," Pace (Apr. 1988), 11:381–383.

(List continued on next page.)

Primary Examiner—Scott Getzow
Attorney, Agent, or Firm—John R. Merkling

[57] ABSTRACT

A pacemaker is disclosed that includes circuitry for monitoring the current and/or voltage delivered to the heart during a pacing pulse. A microprocessor connects to the monitoring circuitry and analyzes the current (and/or voltage) to determine when capture occurs. When capture occurs, the microprocessor terminates the pacing pulse to save energy. Conversely, if capture does not occur within a predetermined maximum time period, or if the pacing pulse amplitude falls below a predetermined threshold value, the processor immediately causes a safety pulse to fire to insure a regular beating of the heart. By monitoring the current and/or voltage delivered, and by permitting the pacing pulse width to be variable, the pacemaker of the present invention can closely track the pacing threshold of the patient with a minimum expenditure of energy.

36 Claims, 5 Drawing Sheets

OTHER PUBLICATIONS

G. Feld, C. Love, J. Camerlo and R. Marsella, "A New Pacemaker Algorithm for Continuous Capture Verification and Automatic Threshold Determination: Elimination of Pacemaker Afterpotential Utilizing a Triphasic Charge Balancing System," *PACE* (Feb. 1992) 15:171–178.

Feuer, J., J. Florio, and A. Shandling, "Alternate Methods for the Determination of Atrial Capture Threshold Utilizing the Telemetered Intracardiac Electrogram," *PACE* (Oct. 1990), 13:1254–1260.

Livingston, A., F. Callaghan, C. Byrd, J. Heemels, P. Hollander, R. Van Mechelen, and J. Chappin, "Atrial Capture Detection with Endocardial Electrodes," *PACE* (Nov. 1988, Part II), 11:1770–1776.

Preston, T. and D. Bowers, "Clinical Applications of the Threshold Tracking Pacemaker," *The American Journal of Cardiology*, 36:322–326.

Schaldach, Max, "Automatic Adjustment of Pacing Parameters Based on Intracardiac Impedance Measurements," *PACE* (Dec., Part II, 1990), 13:1702–1710.

PACEMAKER WITH INTRA-STIMULUS CAPTURE DETECTION

BACKGROUND OF THE INVENTION

The present invention relates generally to pacemakers. More particularly, the present invention relates to an implantable pulse generator for stimulating the heart that uses a minimum amount of energy while insuring regular pacing of the heart. More particularly, the present invention relates to an implantable pulse generator that is capable of automatically adjusting the duration of a pacing pulse based upon detecting capture of the heart.

FIELD OF THE INVENTION

In the normal human heart, the sinus node generally located near the junction of the superior vena cava and the right atrium constitutes the primary natural pacemaker by which rhythmic electrical excitation is developed. The cardiac impulse arising from the sinus node is transmitted to the two atrial chambers (or atria) at the right and left sides of the heart. In response to this excitation, the atria contract, pumping blood from those chambers into the respective ventricular chambers (or ventricles). The impulse is transmitted to the ventricles through the atrioventricular (A-V) node, and via a conduction system comprising the bundle of His, or common bundle, the right and left bundle branches, and the Purkinje fibers. In response, the ventricles contract, the right ventricle pumping unoxygenated blood through the pulmonary artery to the lungs and the left ventricle pumping oxygenated (arterial) blood through the aorta and the lesser arteries to the body. The right atrium receives the venous (unoxygenated) blood from the upper part of the body (head, neck and chest) via the superior vena cava, or upper great vein. The blood oxygenated by the lungs is carried via the pulmonary veins to the left atrium.

This action is repeated in a rhythmic cardiac cycle in which the atrial and ventricular chambers alternately contract and pump, then relax and fill. One-way valves along the veins, between the atrial and ventricular chambers in the right and left sides of the heart (the tricuspid valve and the mitral valve, respectively), and at the exits of the right and left ventricles (the pulmonary and aortic valves, respectively) prevent backflow of the blood as it moves through the heart and the circulatory system.

The sinus node is spontaneously rhythmic, and the cardiac rhythm originating from the primary natural pacemaker is termed sinus rhythm. This capacity to produce spontaneous cardiac impulses is called rhythmicity, or automaticity. Some other cardiac tissues possess this electrophysiologic property and hence constitute secondary natural pacemakers, but the sinus node is the primary pacemaker because it has the fastest spontaneous rate. The secondary pacemakers tend to be inhibited by the more rapid rate at which impulses are generated by the sinus node.

The resting rates at which sinus rhythm occurs in normal persons differ from age group to age group, generally ranging between 110 and 150 beats per minute ("bpm") at birth, and gradually slowing in childhood to the range between 65 and 85 bpm usually found in adults. The resting sinus rate (hereinafter termed simply the "sinus rate") varies from one person to another, and despite the aforementioned usual adult range, is generally considered to lie anywhere between 60 and 100 bpm (the "sinus rate range") for the adult population.

A number of factors may affect the rate of sinus rhythm within the sinus rate range, and some of those factors may slow or accelerate the rate sufficiently to take it outside the sinus rate range. The slower rates (below 60 bpm) are called sinus bradycardia, and the higher rates are termed sinus tachycardia. In particular, sinus tachycardia observed in healthy persons arises from various factors which may include physical or emotional stress (exercise or excitement), consumption of beverages containing alcohol or caffeine, cigarette smoking, and ingestion of certain drugs. The sinus tachycardia rate usually ranges between 101 and 160 bpm in adults, but has been observed at rates up to (and in infrequent instances, exceeding) 200 bpm in younger persons during strenuous exercise.

Sinus tachycardia is sometimes categorized as a cardiac arrhythmia, since it is a variation from normal sinus rate range. Arrhythmia rates which exceed the upper end of the sinus rate range are termed tachyarrhythmias. Healthy persons usually experience a gradual return to the sinus rate after removal of the factor(s) giving rise to sinus tachycardia, and hence, treatment of the arrhythmia is not necessary unless it is found to be attributable to disease. Abnormal arrhythmias (which are hereinafter simply termed "arrhythmias", and in the case of abnormal tachyarrhythmias, simply termed "tachyarrhythmias", to mean arrhythmias associated with cardiac or other disease), however, may require special treatment, and in some instances require immediate emergency treatment toward preventing sudden death of the afflicted individual.

The electrophysiologic properties of the heart include excitability and conductivity, as well as the aforementioned rhythmicity. It has been observed that alteration or impairment of any of these interrelated properties may result in cardiac arrhythmias. For example, A-V junctional tachycardia is an acceleration of the ectopic automaticity that may occur despite the generation of cardiac impulses at the sinus rate by the sinus node.

Excitability, which is the property of cardiac tissue to respond to a stimulus, varies with the different periods of the cardiac cycle. There is an inability of the cardiac tissue to respond to a stimulus during the portion of the refractory period termed the absolute refractory phase (approximating the interval of contraction, from the start of the QRS complex to the commencement of the T wave of the electrocardiogram), and a lower than usual response during another portion of the refractory period constituting the initial part of the relative refractory phase (coincident with the T wave). In the mid-portion of the relative refractory phase corresponding to the top of the T wave, referred to as the vulnerable period, the heart is prone to develop fibrillation in response to even a low intensity stimulus. Fibrillation is a tachyarrhythmia characterized by the commencement of completely uncoordinated random contractions by sections of conductive cardiac tissue of the affected chamber, quickly resulting in a complete loss of synchronous contraction of the overall mass of tissue and a consequent loss of the blood-pumping capability of that chamber.

Excitability of the various portions of the cardiac tissue differs according to their degree of refractoriness, with ventricular tissue being more refractory than atrial tissue and less refractory than A-V junctional tissue, for example. Similarly, the different portions of the heart vary significantly in conductivity, a related electrophysiologic property. For example, ventricular tissue is less conductive than A-V junction tissue.

Disruption of the natural pacemaking and propagation system as a result of aging or disease is commonly treated by artificial cardiac pacing, by which rhythmic electrical discharges are applied to the heart at a desired rate from an implanted artificial pacemaker (referred to throughout the remainder of this document simply as a "pacemaker"). In its simplest form, the pacemaker consists of a pulse generator powered by a self-contained battery pack, and a lead including at least one stimulating electrode(s) for delivery of electrical impulses to excitable myocardial tissue in the appropriate chamber(s) in the right side of the patient's heart. However, in some instances epicardial electrodes are implanted by surgically splitting the patient's chest or other well known techniques, and suturing or screwing them in to the epicardium. Typically, the pulse generator is surgically implanted in a subcutaneous pouch in the patient's chest. In operation, the electrical stimuli are delivered to the excitable cardiac tissue via an electrical circuit that includes the stimulating and reference electrodes, and the body tissue and fluids.

A pacemaker operates in one of three different response modes, namely, asynchronous (fixed rate), inhibited (stimulus generated in absence of specified cardiac activity), or triggered (stimulus delivered in response to specified cardiac activity). The demand ventricular pacemaker, so termed because it operates only on demand, has been the most widely used type. It senses the patient's natural heart rate and applies stimuli only during periods when that rate falls below the present pacing rate.

Pacemakers range from the simple fixed rate device that provides pacing with no sensing function, to the highly complex model implemented to provide fully automatic dual chamber pacing and sensing functions. The latter type of pacemaker is the latest in a progression toward physiologic pacing, that is, the mode of artificial pacing that restores cardiac function as much as possible toward natural pacing.

As shown in FIG. 1, a pacemaker 12 includes stimulating, sensing and processing circuitry, collectively shown as item 26 in FIG. 1. The stimulating portion of circuitry 26 includes a pulse generator that periodically stimulates the heart to insure regular beating of the heart chambers. The sensing circuitry comprises electrical circuits that are controlled by processing circuitry, such as a central processing unit (CPU) or microprocessor. Because of the implementation of the microprocessor in the pacemaker, the pacemaker can be programmed by a physician through an external device 10 to customize the operation of the device to the patient's conditions. As shown in FIG. 1, the pacemaker or other implantable device 12 includes a coil antenna 30 which is capable of communicating through electromagnetic waves to a coil antenna 24 in the external programmer/reader 20 in the external device 10. The pacemaker can be programmed after it is implanted in the patient 14 through electromagnetic signals transmitted by the external programmer. The pacemaker 12 attaches to the patient's heart 16 through electrical leads 18. The pacemaker also includes a communications interface 28 to transmit and receive signals through an antenna 30. Similarly, the external device 10 also includes a communications interface 22 connected to antenna 24.

The pacemaker circuitry typically is powered by a battery pack 35 that is surgically implanted at the same time as the pacemaker. When the battery pack 35 reaches the end of its useful life, it must be either replaced or recharged. If the battery pack 35 must be replaced, another surgical procedure is necessary to make the replacement. Power consumption of pacemaker circuitry, therefore, is critical. Conservation of power can significantly extend the life of the battery, thus delaying the need for additional surgical measures.

One of the critical pacemaker components with respect to power consumption is the pulse generator. In the demand-type pacemakers, the sensing circuitry monitors the pacing activity of the heart, and if regular heartbeat activity is not sensed by the sensing circuitry, the pulse generator delivers a charge to the heart. The amount of charge delivered to the heart is defined by the amplitude and pulse width of the charge, as will be apparent to one skilled in the art. Thus, the greater the amplitude, or the longer the pulse, the more charge that will be delivered to the heart. The amount of charge to be delivered is determined by the "pacing threshold," which is the amount of charge required to stimulate the chambers of the heart of that particular patient. The amplitude of the charge delivered by the implantable pulse generator, therefore, typically can be varied by the physician to customize the pacing charge generated by the pulse generator to the pacing threshold of a particular patient. In most instances, the pulse width is fixed, and cannot be varied. Thus, during implant, the pacing threshold of the patient's heart is measured, and the amplitude of the charge delivered by the pulse generator is selected to insure a response by the heart. Subsequently, the physician or technician will measure the pacing threshold during follow-up visits by the patient, and may re-program the pulse generator to increase or decrease the amplitude of the pacing charge delivered by the pulse generator.

One problem with setting the pacemaker with a predetermined pacing charge is that the pacing threshold of a patient changes over time. The pacing threshold may change for any number of reasons, including maturation of the lead connecting the pulse generator to the heart, the time of day (referred to as "circadian variation"), exercise level, stress level, pacing rate, age and ongoing disease processes. Tests have shown that shortly after implant, the pacing threshold increases as the conductive leads connecting the pacemaker to the heart mature. Thus, as shown in FIG. 5, for example, the leads 38, 39 are encapsulated with fluids and secretions generated by the body. This coating of the leads in the vicinity of the heart causes increased resistance, which translates to a higher pacing threshold to stimulate the heart. After a few months, the pacing threshold then typically drops, absent some deteriorating condition.

As the example of FIG. 2 illustrates, the average pacing threshold originally was approximately 0.6 volts, but within one to four weeks, increased to approximately 2.0 volts as the leads mature. The threshold then stabilizes to approximately 1.5 volts. In addition to looking at the average pacing threshold over an extended period of time, it is also beneficial to consider the variations in pacing threshold that occur during the different portions of the day. As shown in the example of FIG. 3, the pacing threshold may fluctuate during the course of the day, depending upon the physical activity of the patient. Thus, during periods of sleep the pacing threshold may be higher than during waking hours, for example. Despite these general propositions regarding pacing thresholds, experience has shown that pacing thresholds vary widely from patient to patient, and thus it is difficult to develop a fixed routine for tracking pacing threshold for a particular patient.

Because of the expectation that the pacing threshold will change, the physician typically programs a "safety margin" into the pacemaker to insure that the pacing charge delivered by the pulse generator exceeds the pacing threshold of the patient. Thus, the physician normally programs the pulse generator with a greater amplitude than was indicated by the pacing threshold measured during implant. As shown in the examples of FIGS. 2 and 3, the pacing charge is set at a relatively high level to provide a safety margin above the pacing threshold.

The problem with this "supra-maximal" approach is that energy is wasted in a device that has a limited power supply. In addition, the conventional approach of simply setting the pacing charge high ignores the true pacing threshold of the heart, and thus raises the possibility that the heart may not respond to the pacing charge (the heart fails to "capture"). Thus, for example, if the patient is placed on medication, the possibility exists that the patient's pacing threshold will become greater than the pacing charge. As a result, the heart fails to capture even though the pacing charge amplitude included a safety margin.

Various systems have been proposed to overcome these problems. These approaches commonly are referred to as "capture verification" or "auto-capture" systems. As the name implies, capture verification systems attempt to detect or verify whether the pacing pulse actually achieved stimulation of the myocardium. The capture verification systems also seek to have the pacemaker automatically determine the pacing threshold.

More recently pacemakers have been proposed which monitor the heart to determine if capture occurred in response to a pacing stimulus. These devices typically deliver a pulse of a fixed width and then look for an indication of capture after delivery of the pulse. These auto capture systems then periodically (at certain programmed intervals) reduce the pacing charge until capture is lost, as determined by the capture verification system. Once capture is lost, the auto capture algorithms generate a higher energy safety pulse to insure that the heart paces. The pacing charge then is set at an amplitude level that is slightly greater than the charge which failed to result in a capture.

In these type of systems, the pacing pulse is generated and the system monitors the heart for a response. Responses may include (1) the detection of the ventricular evoked response; (2) changes of intra-cavitary impedance caused by the ventricular volume decreasing as the ventricle contracts; and (3) changes of intra-cavitary pressure as the ventricle contracts. If no response occurs between 50-150 milliseconds (ms) after the pacing pulse, a higher amplitude safety pulse is generated. Thus, to determine the pacing threshold of the patient, it is necessary to lower the pacing pulse to an amplitude which results in the heart not capturing, and then generating a high amplitude second safety pulse. Because these systems must generate the second pulse to determine the pacing threshold, additional energy is expended which could result in using more energy than the system saves by attempting to track the pacing threshold. Furthermore, because these systems require loss of capture to detect the pacing threshold, the heart is required to experience an irregular rhythm as the heartbeat is delayed while the system determines if the heart captured. The heart in essence undergoes a hiccup, which even a novice to this art will appreciate is not desirable in patients already suffering from heart problems.

Thus, existing threshold tracking algorithms require loss of capture before adjustments are made. In addition, the present techniques for capture verification are based on measuring either an electrical or mechanical consequence of capture. This requires that the system wait for the consequence to occur, which could take up to 150 milliseconds (ms) after the pacing pulse. Thus, there is a significant delay before the detection system can make the decision that a failure occurred and insert a safety pace. This can result in up to 150 ms of extra ventricular filling time, which would be terminated either by the ventricular safety pace or a ventricular ectopic site firing. The patient would feel this as an extra strong pulse, or palpitation.

It would be desirable if a capture detection system could be developed to minimize the pacing charge to the minimal charge necessary to stimulate the heart. By minimizing the pacing charge, the life of the pacemaker battery can be extended. It also would be desirable to develop a system in which the stimulating circuitry was cognizant of whether capture has occurred during the period that the pacing stimulus pulse is delivered. It also would be desirable if an auto-capture methodology could be developed which would insure a capture very quickly during the adjusting of the pacing charge to eliminate stress on the heart. Despite the apparent advantages of such a system, to date no one has developed a system capable of alleviating these deficiencies.

SUMMARY OF THE INVENTION

The present invention solves the shortcomings and deficiencies of the prior art by constructing a pacemaker which is capable of simultaneously measuring the current and/or voltage during a pacing pulse. By measuring the current and voltage, the pacemaker circuitry can analyze the conductance, impedance, and energy that is delivered to the heart. Thus, if the measured voltage, current, or impedance dips or undergoes an inflection, the pacemaker circuitry can determine if capture has occurred. In the event that capture does not occur, the pacemaker circuitry can generate a safety pulse without the long delay required in the prior art systems.

In accordance with the preferred embodiment of the present invention, the width of the pacing pulse may be varied independently or together with the amplitude of the pacing pulse. Thus, the duration of the pacing pulse may be varied until capture occurs, or until the system determines that capture will not occur. In addition, the present invention uses the capture detection to terminate the pacing pulse to minimize the energy expended by the system.

The present invention includes pulsing circuitry that generates a pacing pulse with an initial voltage amplitude which is delivered to the heart. Monitoring circuitry measures the current and/or voltage delivered to the heart. The monitoring circuitry, in conjunction with processing circuitry, determines when capture occurs, at which time the pacing pulse is terminated. If the voltage of the pacing pulse falls below a threshold value before capture occurs, the pacing pulse is terminated and a safety pulse is immediately delivered. Similarly, if the duration of the pacing pulse exceeds a maximum period, the pulse is terminated and the safety pulse is immediately delivered. If a safety pulse is delivered, subsequent pacing pulses will be modified to have a higher initial voltage amplitude. According to one embodiment of the invention, the amplitude of the pacing pulse may be modified even in the event of capture. Thus, if the heart captures relatively soon in the pacing pulse, the processing circuitry may lower the initial voltage amplitude of subsequent pulses. Conversely, if capture was detected very late in the pacing pulse, the initial voltage amplitude may be increased. Thus, the pacing pulse may be modified without requiring capture failure.

These and other advantages of the present invention will become apparent upon reading the disclosure which follows.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENT

Figure 5:
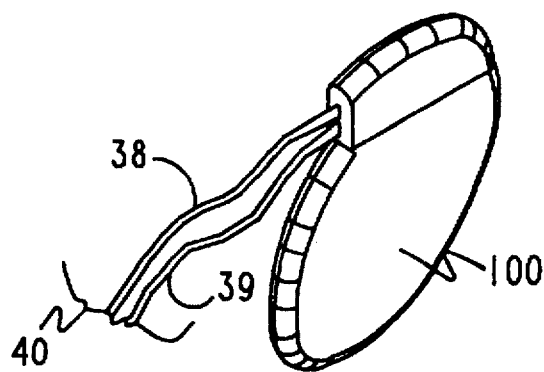
FIG. 5 is an illustration of a typical pacemaker which may be used in conjunction with the present invention.

Referring initially to FIG. 5, a pacemaker 100 connects to the wall 40 of the patient's heart 40 to deliver electrical pacing stimulus pulses that insure regular beating of the heart. In the preferred embodiment, the pacemaker delivers the pacing pulse via two conductive leads 38, 39. As one skilled in the art will understand, however, greater or fewer leads may be provided for delivering the pacing stimulus to the heart. Leads 38, 39 are insulated in accordance with techniques well known in the art. The following discussion focuses on the generation and modification of the pacing pulse to insure a response by the heart ("capture"), while expending the minimum amount of energy necessary to extend the battery life, and thus delay the need for subsequent surgical measures. Other details regarding the pacemaker, including the use of the pacemaker for other purposes such as defibrillation, are omitted for the sake of clarity, and so as not to obscure the present invention.

Figure 6:
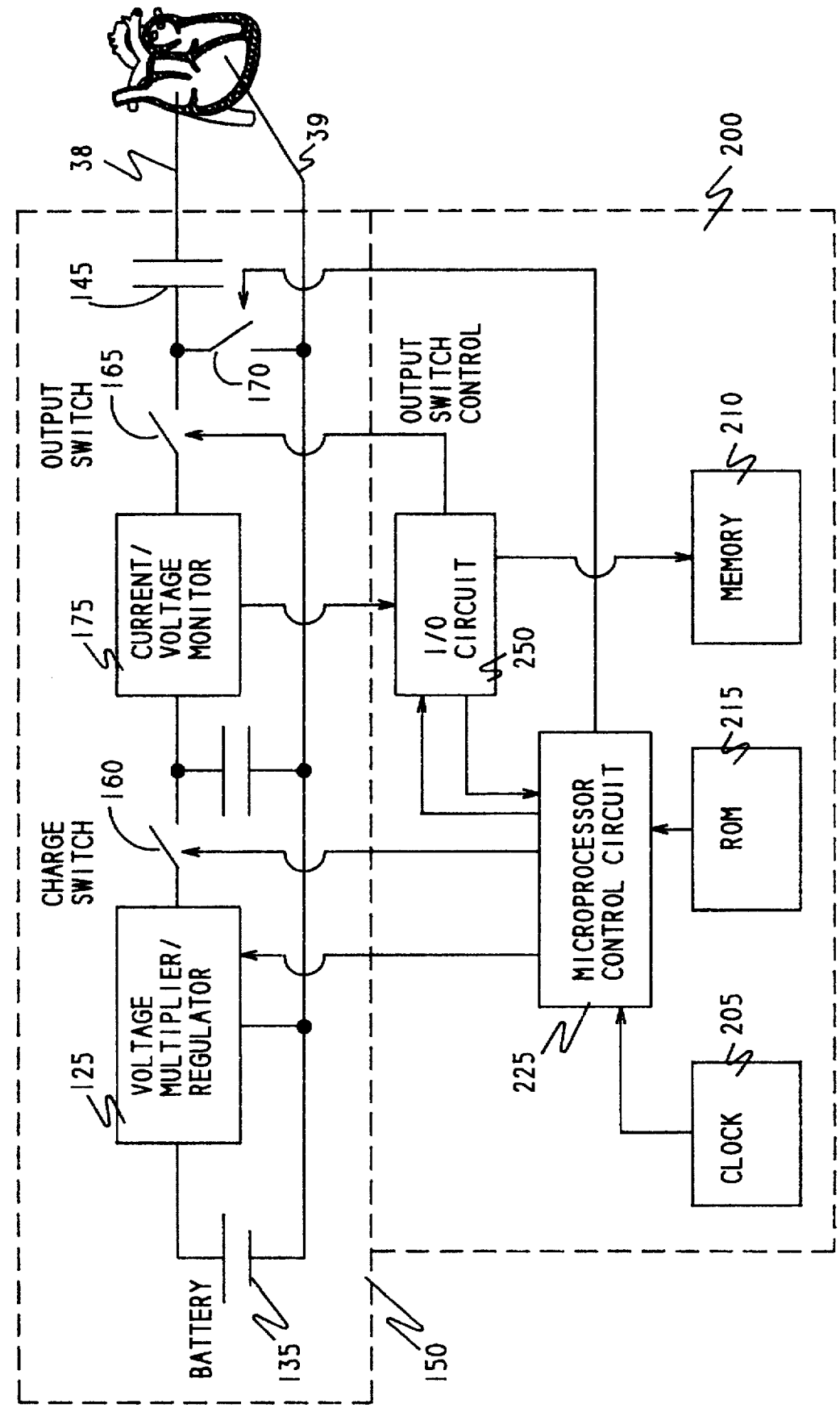
FIG. 6 is a schematic block diagram of the pulse generator and processing circuitry of the present invention.

Referring now to FIG. 6, the pacemaker 100 constructed in accordance with the preferred embodiment generally includes pulse generating and sensing circuitry 150 and control circuitry 200. The pulse generating and sensing circuitry 150 preferably generates pacing pulses under the control of the control circuitry that are delivered to the heart to stimulate the heart to beat. As one skilled in the art will understand, the pulse generating and sensing circuitry 150 and the control circuitry 200 may be used to provide other system functions in addition to regulating pacing activity.

Referring still to FIG. 6, the pulsing and sensing circuitry 150 preferably includes a voltage multiplier/regulator circuit 125 coupled to a battery pack or cell 135, a storage capacitor 140 and a coupling capacitor 145, a charge switch 160, an output switch 165, a termination switch 170, and a current/voltage monitoring circuit 175. It should be understood that while the pulsing circuitry and sensing circuitry are referred to in integrated fashion in this disclosure, the two circuits could be separated and referred to independently. The pulsing and sensing circuitry 150 (which may be referred to herein as just the "pulsing circuitry") functions to generate and deliver a pacing pulse to the heart via leads 38, 39. In accordance with the preferred embodiment, the pulsing and sensing circuitry also preferably senses the current and/or voltage delivered to the heart via leads 38, 39 in order to determine whether the heart has responded to the electrical stimulus (i.e., whether the heart has captured).

The battery 135 preferably comprises the main battery pack for the pacemaker 100. Thus, although not shown specifically, the battery pack 35 also provides operating power to the electronic components included in the pacemaker 100. The battery pack 35 provides a fixed voltage signal for use by the pulsing circuitry 150 which is modified by the voltage multiplier/regulator circuitry 125. Thus, in accordance with known techniques, the multiplier/regulator circuitry 125 either multiplies or regulates the voltage provided by the battery pack 135. The voltage multiplier/regulator 125 receives a control signal from the main control circuit 225 which specifies the output voltage to be delivered by the multiplier/regulator 125. If a multiple of the battery voltage is required as the pacing pulse, the control circuit 225 provides a suitable control signal to the voltage multiplier/regulator 125 which causes multiplier/regulator 125 to multiply the voltage input by a predetermined amount to deliver a multiplied voltage as an output. Voltage regulation of the battery pack voltage occurs in similar fashion, except that the output from the multiplier/regulator 125 is a percentage of the battery voltage. In the preferred embodiment, the multiplier/regulator 125 has a number of available voltage outputs (some of which are multiples and some of which are fractions of the battery voltage) to provide flexibility in the voltage amplitude of the pacing pulse delivered by the pulsing circuitry. Thus, for example, ten different voltage amplitude outputs may be available from the multiplier/regulator 125, thus providing ten different possible voltage amplitudes for the pulsing circuitry.

Referring still to FIG. 6, the voltage output from the multiplier/regulator 125 charges the storage capacitor 140 if the charge switch 160 is closed. The status of switch 160 is controlled by a signal from the control circuit 225. In the preferred embodiment, the charge switch 160 connects electrically to the output of the multiplier/regulator 125, and the anode of the storage capacitor 140 connects to charge switch 160. The cathode of capacitor 140 connects to ground. The storage capacitor 140 generates the pacing pulse, based upon the opening and closing of switches 160, 165 and 170 by the control circuit 225. While a single storage capacitor 140 is shown in FIG. 6, it should be understood by one skilled in the art that multiple capacitors may be provided.

A voltage/current monitor 175 couples to the anode of the storage capacitor 175 to monitor the current and/or voltage delivered by the storage capacitor 160. The monitor 175 provides an electrical signal representing the sensed current and/or voltage to the control circuit 200 via an input/output (I/O) circuit 250, which relays the signal to the control circuit 225 after appropriate conditioning.

Referring still to FIG. 6, an output switch 165 couples the anode of storage capacitor 140 to the anode of coupling capacitor 145. The cathode of coupling capacitor 145 preferably couples to conductive lead 38. In accordance with the preferred embodiment, the status of the output switch 165 is controlled by the control circuit 225. When the output switch 165 is closed, the pacing pulse is transmitted by the leads 38, 39 to the heart. When the switch 165 is opened, the storage capacitor is disconnected from leads 38, 39, thus terminating the pacing pulse. In the preferred embodiment, a termination switch 170 also couples across the leads 38, 39 (between the anode of coupling capacitor 145 and ground). The status of termination switch 170 is controlled by the control circuit 225. Closing the termination switch 170 causes a short circuit path preventing further charging of the coupling capacitor 145.

Referring still to FIG. 6, the control circuitry 200 preferably includes a control circuit 225 and an input/output circuit 250. The control circuit 225 preferably comprises a digital control section comprising a microprocessor for storing and executing software instructions and for storing and processing the data for all digital functions of the pacemaker 100, including detection, processing, timing, switching, control and other functions. As an alternative, an application specific integrated circuit (ASIC) may be designed which performs the required functions of the control circuit 225. An analog I/O circuit section 250 also is preferably provided as part of the control circuitry 200 for monitoring the patient's EKG signal information over each cardiac cycle, enhancing that signal information while eliminating noise and other interference through signal filtering and automatic gain control, and controlling the closing and opening of output switch 165 (and thus the initiation and termination of the pacing pulse) under the direction of the microprocessor control circuit 225. Power for the control circuitry preferably is provided by battery pack 135 and other components (not shown) for regulating the power supply to an acceptable level.

The microprocessor in the main control circuit 225 preferably can be programmed to receive initial parameters from a physician regarding the desired pacing voltage amplitude, and other parameters as will be apparent to one skilled in the art. The microprocessor control circuit 225 preferably includes a read only memory (ROM) device 215 for storing the initial programming parameters, and instructions for modifying initial parameters based upon values sensed by the pulse generating and sensing circuitry 150. The control circuit 200 also preferably includes a clock 205 connected to the microprocessor control circuit 225 to enable the control circuit 225 to determine when a pacing pulse is required in the absence of a regular heartbeat. The clock 205 provides regular clock signals to the microprocessor control circuit 225 which accumulates the clock signals and compares the accumulated clock signal with a predetermined value representing the desired interval between heart beats. The predetermined beat interval value preferably is stored in the ROM 215.

The input/output circuit 250 connects electrically to the main control circuit 225, and preferably conditions signals received from the monitor circuitry 175. Thus, for example, the input/output circuit 250 may include an analog-to-digital converter (ADC) for converting analog signals into digital signals before the signals are relayed to the microprocessor in the main control circuit 225. As one skilled in the art will understand, the input/output circuit 250 may be integrated as part of the microprocessor control circuit by providing the conditioning circuitry, conversion circuitry and output circuitry as part of the microprocessor. In one embodiment of the invention, the input/output circuit 250 saves a digital representation of the monitored current (or voltage) signal directly into a memory device 210, which can subsequently be downloaded for purposes of analyzing the pacing threshold. Alternatively, the memory device 210 may connect to the microprocessor control circuit 225 to permit the microprocessor to compress the monitored data to save space in memory. As one skilled in the art will understand, the functions of memory 210 and ROM 215 may be combined together in a unified memory.

The operation of the microprocessor control circuit 225 will now be described in accordance with the preferred embodiment. Before discussing the routine implemented by the microprocessor, the analysis of the monitored current and/or voltage signals will be discussed. The microprocessor control circuit 225 receives signals from monitoring circuitry 175 permitting the microprocessor to analyze the current and/or voltage delivered by the storage capacitor 140 to determine when capture occurs. The microprocessor preferably analyzes both current and voltage values independently, as well as looking at ratios of the current and voltage and the product of the current and voltage values. In the past, capture verification processes applied a voltage for a fixed amount of time with the hope that the voltage would generate enough current to stimulate the heart muscle. The present invention monitors the current delivered to the heart as a diagnostic tool, which together with the voltage, provides information permitting the microprocessor to instantaneously determine when capture occurs.

The interface between the lead and the heart resembles an RC (resistor and capacitor) network. At the cellular level, the interface looks like a conducting fluid with a cell membrane. When the heart initiates a contraction in response to an electrical stimulus, ion channels open to allow sodium and potassium to flow. Thus, if the voltage of the pacing pulse remains steady, the current delivered to the heart provides an indication of whether the ion channels have begun to flow. If the current resembles a passive circuit, then the heart has not captured, and the pulse is ineffective. If a deflection appears in the current waveform, that is an indication that capture has occurred.

Thus, according to the preferred embodiment, deflections (or inflections) in the current, voltage or other electrophysiological parameters could indicate capture because capture is accompanied by a cascade of cellular membrane ion channels opening. Capture and the ionic cascade that follows is an active process. In addition to measuring a capture inflection, other decision criteria may include the total or peak energy delivered, the mean or minimum impedance during the pulse, the phasic variations between the current and voltage during the pulse, and many other electrical phenomenon.

Figure 1:
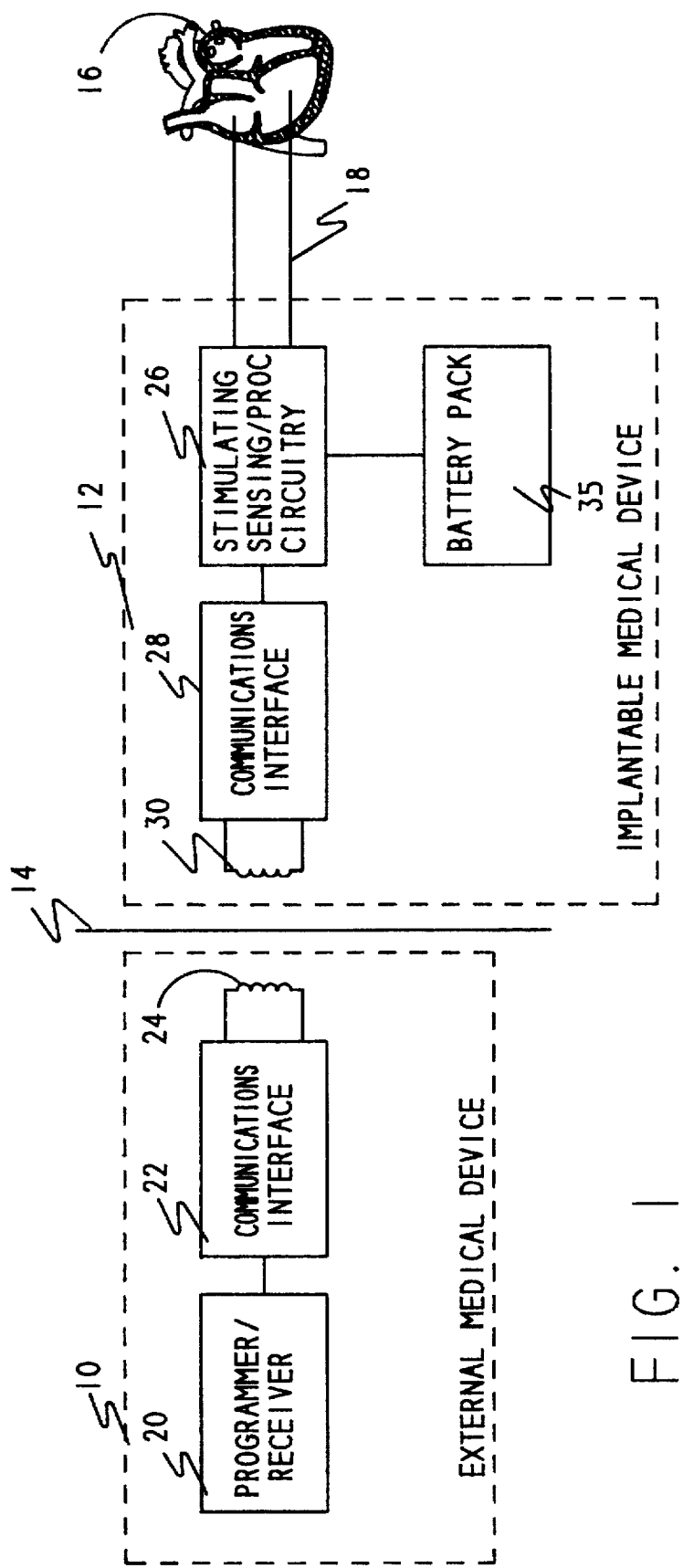
FIG. 1 is a functional block diagram illustrating a pacemaker and associated electronic circuitry.
Figure 2:
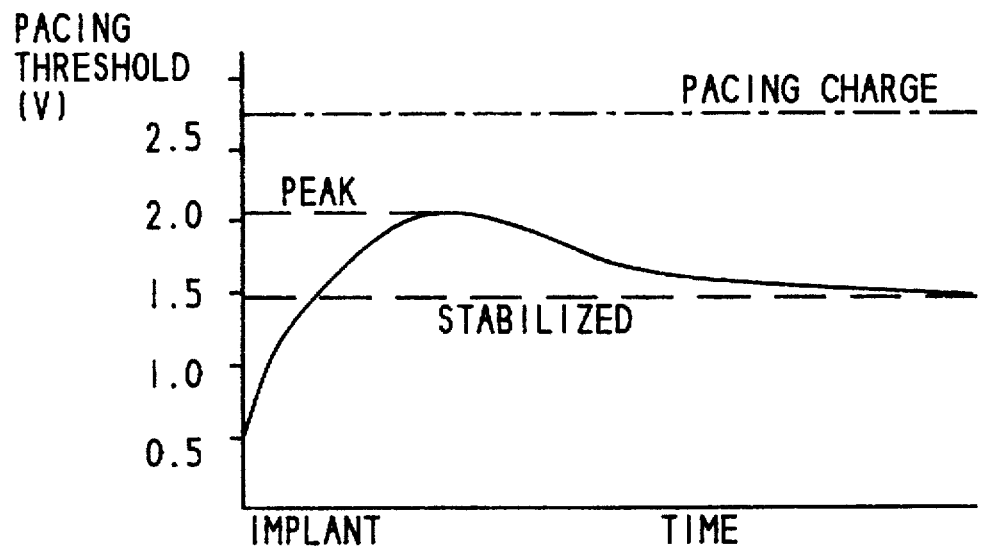
FIG. 2 is an exemplary chart depicting fluctuations in pacing threshold of a heart over the life of a pacemaker.
Figure 3:
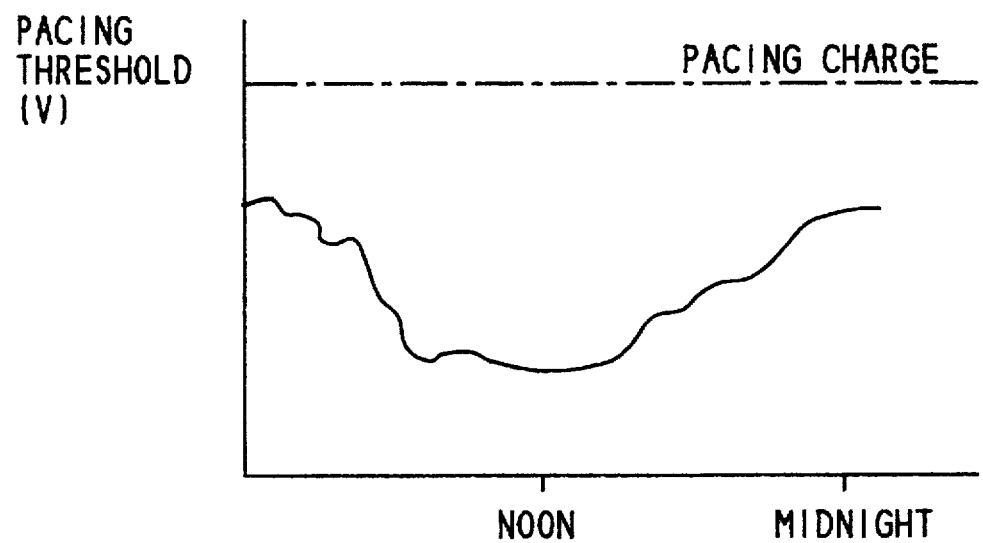
FIG. 3 is an exemplary chart depicting fluctuations in pacing threshold of a heart over a twenty four hour cycle.
Figure 4A:
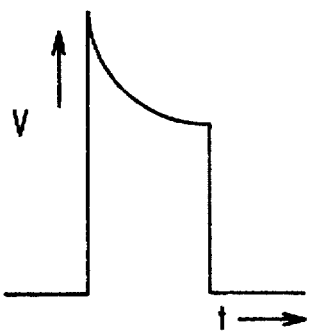
FIGS. 4A–D depict exemplary voltage and current diagrams depicting the pacing pulse and expected heart responses which are used to illustrate the principles of the present invention.
Figure 4B:
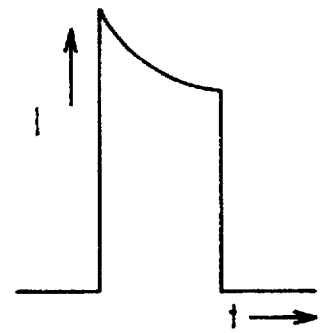
Figure 4C:
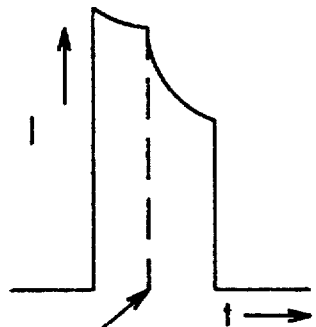
Figure 4D:
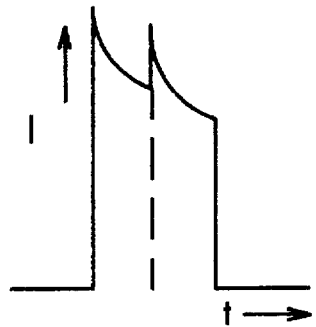

Thus, referring now to FIG. 4A, a representation of a pacing pulse is shown, with a voltage V. The expected current response is shown in FIG. 4B for a heart that fails to capture. Conversely, FIG. 4C shows one possible current response for a heart which captures. The point at which capture first occurred is defined by the first deflection point. FIG. 4D shows a second possible current response indicating capture. As shown in FIG. 4D, the current decreases prior to the capture in accordance with the characteristics of a passive RC circuit. When capture occurs, the current may jump due to the change in permeability from low to high in the heart cell membranes.

Thus, according to the preferred embodiment, the present invention monitors either current or voltage (or preferably both) delivered by the pacing pulse to provide an instantaneous indication of the point in time when capture occurs. The microprocessor control circuit 225 of the present invention may look at current or voltage independently, a ratio of current and voltage for an indication of impedance (or conductance), or a product of the voltage and current for an indication of power. Any or all of these parameters may be analyzed to determine capture. By measuring the instantaneous occurrence of capture, the present invention can provide a much more efficient pacing pulse which closely resembles the pacing threshold.

The present invention permits a pacing pulse to be delivered which minimizes the energy consumed, while insuring capture. This is achieved by providing a pacing pulse with a variable duration, so that the pacing pulse extends until capture occurs. Thus, the microprocessor selects a voltage for the pacing pulse. Thus, for example, a voltage of 2.0 volts may be used as the pulse amplitude. Although not required, the microprocessor may also have an expectation of the necessary duration of the pulse to cause capture. The duration of the pacing pulse is extended until capture occurs, up to some predefined maximum pulse period, such as 1.5 ms. If capture does not occur within the maximum pulse period, a safety pulse is immediately generated, without the long delays that characterize prior art capture verification methods. Because the interface between the leads and the heart resembles a capacitive network, extending the duration of the pulse serves to charge the interface until the pacing threshold is reached, at which time the heart is stimulated and capture occurs.

Thus, in the preferred embodiment, the duration of the pacing pulse is flexible. This permits variation of the pulse duration, and thus the energy delivered to the heart, without requiring modification of the voltage amplitude of the pacing pulse. In one embodiment of the present invention, the microprocessor can analyze the point of capture to determine if the initial voltage amplitude of the pacing pulse may be varied. Thus, if the period for capture extends to a point close to the maximum period, then the amplitude of the pulse may be increased to avoid the need to fire a safety pulse. Conversely, the amplitude may be decreased if capture occurs very quickly in response to the pacing pulse. Thus, ranges may be set up based upon the duration of the pulse required for capture. If capture occurs in a time period less than x, then the amplitude of subsequent pacing pulses is decreased. If capture occurs in a time period greater than y, then the amplitude of the pacing pulse is increased for subsequent pulses. Thus, for example, if capture occurs within 0.15 ms of pulse origination, then the voltage amplitude may be decreased one level for subsequent pacing pulses. If capture does not occur until 1.25 ms of pulse origination, then the voltage amplitude may increased on level for subsequent pacing pulses. Lastly, if capture does not occur until 1.5 ms after pulse origination, then the pulse is terminated, a safety pulse is fired, and the voltage amplitude for the pulse is increased.

The voltage delivered by the pacemaker 100 resembles a rectangular hyperbole, and exhibits an RC exponential decaying voltage, defined by the Lapique equation, as follows:

$$V = R + b/t$$

where

V is the voltage delivered by the stimulus circuitry,

R is the Rheobase, b is the chronaxis, and t is the pulse period.

As the pulse period increases, the voltage delivered by the pulsing circuitry 150 approaches the Rheobase value, and the possibility of capture decreases. Thus, in accordance with the preferred embodiment, a safety margin is added into the initial voltage to insure capture. The safety margin may be based on a multiple of the expected energy required for capture, a multiple of the charge delivered, or various other parameters or combinations of parameters, as desired. In addition, the microprocessor terminates the pacing pulse and fires the safety pulse as the monitored voltage approaches the Rheobase, based upon the increasing likelihood that capture will not occur.

Figure 7:
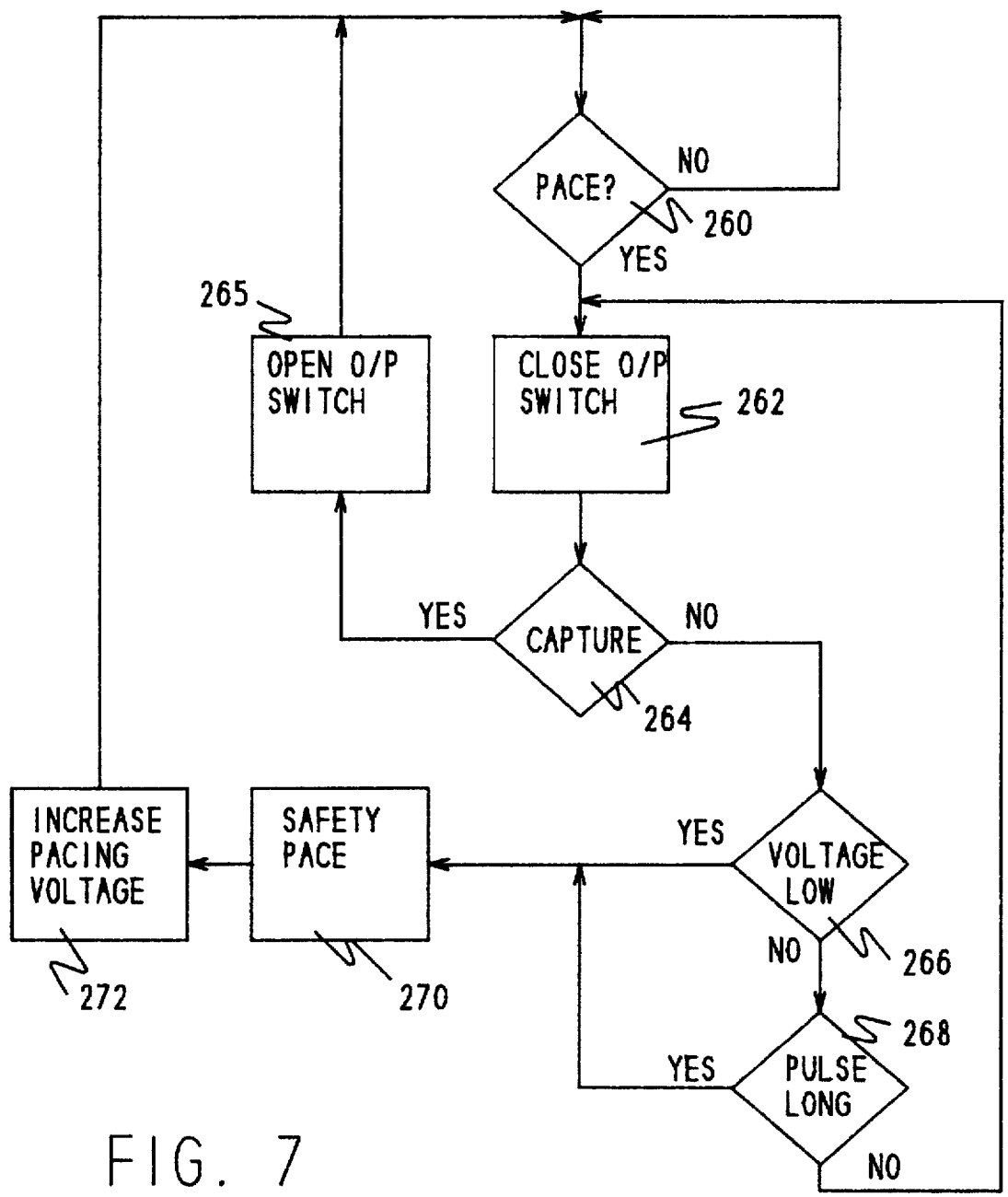
FIG. 7 is a flow chart illustrating the operation of the control circuit of FIG. 6.

The preferred operation of the microprocessor will now be described. Referring to FIGS. 6 and 7, the control circuit 225 begins each pacing cycle by determining in step 260 if a pacing pulse is required due to the clock signal accumulation in the microprocessor. If a pacing pulse is required, the microprocessor control circuit 225 causes the I/O circuit 250 to close the output switch 165 in step 262, causing an electrical pacing pulse to be delivered to the heart. In step 264, the control circuit 225 receives conditioned signals from the current/voltage monitor 175 after conditioning and conversion by the I/O circuit 250, and analyzes the signals (either independently, or in combination) for a deflection in the monitored waveform, or some other indication that capture has occurred. If a deflection is detected in step 264, the processor proceeds to step 265. If capture is not detected in step 264, then the processor proceeds to step 266. In response to capture detection, the processor control circuit 225 causes the output switch 165 to open, and further causes termination switch 170 to close. If desired, an additional step may also be provided to increase the pacing pulse amplitude if the processor determines that the period to capture was excessive.

If capture is not detected in step 264, the processor control circuit 225 determines if the voltage amplitude of the pacing pulse is too low in step 266. If the amplitude of the pulse falls below a predetermined threshold (which preferably is defined within a predetermined value of the Rheobase, or as a fixed value such as 1.0 volts), the processor assumes that the pacing pulse will not result in capture. If the pulse falls too low, the processor initiates a safety pulse in step 270, and the voltage amplitude is increased for the next pacing pulse. If the voltage is not too low, the processor determines if the pulse has reached the maximum pulse duration in step 268 (such as, for example, 1.5 milliseconds). If the pulse has reached the maximum period, the processor proceeds to step 270 and fires the safety pulse. The voltage then is increased for subsequent pacing pulses. In the preferred embodiment, the safety pulse is fired as soon as possible after a determination is made that capture has not occurred to insure a rhythmic beating of the heart. In addition, by firing the safety pulse immediately following the pacing pulse, the pacing pulse serves to precharge the heart membrane, making it more likely that the safety pulse will result in capture. If the processor determines that the pulse duration is not excessive, the processor returns to step 262, and the cycle continues until either capture occurs, or the processor determines that capture will not occur based upon predetermined criteria.

Thus, in the preferred embodiment, the pacing pulse is generated and is maintained until capture occurs, at which time the pacing pulse is terminated to save energy. Alternatively, the control circuit 225 determines that capture will not occur either because the pulse is too long, or the voltage delivered is too low. In that event, the control circuit 225 causes the safety pulse to immediately fire. Subsequent pacing pulses are then preferably set at the next higher value by modifying the multiplier/regulator circuit 125 to provide a different output voltage.

The algorithm of FIG. 7 may be implemented intermittently to periodically provide capture verification, or may be run continuously as the basic methodology for providing the pacing pulse. In addition, the pacing procedure of FIG. 7 may be used during physician diagnostic operations to determine pacing threshold. Further, the algorithm may also be modified to provide that the voltage amplitude could be reduced if capture occurs extremely quickly. In the preferred embodiment, capture information preferably is stored in memory to permit the physician to download the information and to determine the optimal voltage amplitude setting. In addition, if capture is not occurring, various other treatments may be required.

The present invention preferably determines the optimal pacing pulse amplitude voltage for the pacing threshold. A predetermined safety margin may then be added, either in the form of the pulse amplitude or pulse width. An expected width value for the pacing pulse could be derived based upon either a single capture verification measurement, or by averaging a plurality of capture measurements. If a plurality of values are used, the minimum and maximum values could be compared to determine the degree of consistency for selecting a safety factor margin. Thus, if 64 beats were measured, a measured mean value might be 0.25 ms, with a lower and upper range of 0.20 ms and 0.30 ms, respectively. In this example, the expected pulse width might be selected as 0.35 ms, which is the mean plus twice the positive deviation. If the range varied from 0.15 ms to 0.35 ms, then an expected width might be chosen as 0.45 ms. As one skilled in the art will understand and appreciate, different algorithms and safety factors may be selected. As additional pacing studies are performed, the present invention may be optimized to determine the most efficient pulse which still insures heart response.

While a preferred embodiment of the invention has been shown and described, modifications thereof can be made by one skilled in the art without departing from the spirit of the invention.

We claim as our invention:

1. A pacemaker for delivering a pacing pulse to a heart via a conductive lead, comprising:
    a battery for producing an output voltage;
    a voltage multiplier capable of changing the output voltage of the battery to a voltage defining an amplitude for the pacing pulse;
    a storage capacitor coupled to said voltage multiplier for storing the pacing pulse;
    a coupling capacitor connected to a conductive lead;
    an output switch selectively coupling the coupling capacitor to said storage capacitor;
    a control circuit coupled to said output switch for controlling the delivery of the pacing pulse to the heart; and
    monitoring circuitry coupled between said storage capacitor and said heart to measure an electrical parameter of the pacing pulse delivered to the heart, said monitoring circuitry providing a signal representing said electrical parameter to said control circuit, and said control circuit opening said output switch in response to a determination that the heart has responded to the pacing pulse.

2. A pacemaker as in claim 1, wherein the electrical parameter monitored includes a representation of current delivered to the heart.

3. A pacemaker as in claim 1, wherein the electrical parameter monitored includes a representation of voltage delivered to the heart.

4. A pacemaker as in claim 3, wherein the control circuit analyzes the voltage delivered to the heart to determine if the voltage falls below a minimum value before the heart responds.

5. A pacemaker as in claim 4, wherein the control circuit causes a safety pulse to be delivered to the heart in the event that the voltage falls below the minimum value before the heart responds.

6. A pacemaker as in claim 5, wherein the control circuit modifies the amplitude of the pacing pulse if the safety pulse is generated.

7. A pacemaker as in claim 1, wherein the electrical parameter comprises a ratio of current and voltage.

8. A pacemaker as in claim 1, wherein the electrical parameter comprises a product of current and voltage.

9. A pacemaker as in claim 1, wherein the control circuit includes a microprocessor that is programmed with an initial voltage amplitude for the pacing pulse.

10. A pacemaker as in claim 9, wherein the control circuit couples to said voltage multiplier to control the amplitude of the pacing pulse.

11. A pacemaker as in claim 10, further comprising a charging switch connected between the voltage multiplier and the storage capacitor, and said control circuit couples to said charging switch to control the charging of said storage capacitor.

12. A pacemaker as in claim 11, wherein the voltage multiplier also functions as a voltage regulator.

13. A pacemaker as in claim 12, further comprising an input/output circuit connected between said monitor circuit and said control circuit for conditioning the signal representing the electrical parameter.

14. A pacemaker as in claim 13, further comprising a termination switch connected between said coupling capacitor and ground.

15. A pacemaker as in claim 1, wherein the control circuit includes a clock for providing a signal to said control circuit which said control circuit uses to determine when a pacing pulse is required.

16. A pacemaker as in claim 1, wherein the control circuit causes a safety pulse to be generated if the heart fails to respond to said pacing pulse within a maximum time period.

17. A pacemaker as in claim 16, wherein the control circuit modifies the amplitude of the pacing pulse if the safety pulse is generated.

18. A method for stimulating a heart with a pacing pulse, comprising the steps of:
    generating a pacing pulse;
    determining if the heart has responded to the pacing pulse;
    terminating the pacing pulse if the heart responds to the pacing pulse.

19. A method as in claim 18, wherein the step of generating the pacing pulse includes closing an output switch, and the step of terminating the pacing pulse includes opening the output switch.

20. A method as in claim 18, wherein the step of determining if the heart has responded to the pacing pulse includes monitoring the pacing pulse for deflections.

21. A method as in claim 20, wherein the step of monitoring the pacing pulse includes monitoring current delivered to the heart.

22. A method as in claim 21, wherein the step of monitoring the pacing pulse includes monitoring voltage delivered to the heart.

23. A method as in claim 22, wherein the step of monitoring the pacing pulse includes monitoring current delivered to the heart.

24. A method as in claim 23, further comprising the step of generating a safety pulse if the monitored voltage falls below a threshold value before the heart responds.

25. A method as in claim 24, wherein the safety pulse is generated immediately to insure capture of the heart.

26. A method as in claim 18, further comprising the step of generating a safety pulse if a maximum time period expires before the heart responds.

27. A method as in claim 18, wherein the safety pulse is generated immediately to insure capture of the heart.

28. A method for stimulating a heart with a pacing pulse, comprising the steps of:
    generating a pacing pulse;
    monitoring voltage of the pacing pulse;
    monitoring current delivered by the pacing pulse to determine if the heart has responded to the pacing pulse;
    generating a safety pulse if the monitored voltage falls below a threshold value before the heart responds.

29. A method as in claim 28, wherein the step of determining if the heart has responded to the pacing pulse includes monitoring the current of the pacing pulse for deflections.

30. A method as in claim 28, wherein the safety pulse is generated immediately to insure capture of the heart.

31. A method as in claim 28, further comprising the step of generating a safety pulse if a maximum time period expires before the heart responds.

32. A method for stimulating a heart with a pacing pulse, comprising the steps of:

generating a pacing pulse;

monitoring duration of the pacing pulse;

monitoring the pacing pulse to determine if the heart has responded to the pacing pulse;

generating a safety pulse if the duration of the pacing pulse exceeds a maximum period.

33. A method as in claim 32, wherein the step of determining if the heart has responded to the pacing pulse includes monitoring current delivered by the pacing pulse to the heart.

34. A method as in claim 32, wherein the safety pulse is generated immediately to insure capture of the heart.

35. A method as in claim 32, wherein the step of determining if the heart has responded includes monitoring voltage of the pacing pulse.

36. A method as in claim 35, further comprising the step of generating a safety pulse if the monitored voltage falls below a threshold value before the heart responds.

* * * * *